US006436440B1

(12) United States Patent
Meffert et al.

(10) Patent No.: US 6,436,440 B1
(45) Date of Patent: Aug. 20, 2002

(54) USE OF N-VINYLLACTAM-OR-N-VINYLAMINE-CONTAINING COPOLYMERS AS MATRIX FOR PRODUCING SOLID PHARAMACEUTICAL AND COSMETIC PRESENTATIONS

(75) Inventors: Helmut Meffert, Mannheim; Folker Ruchatz, Neustadt, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/283,195

(22) Filed: Apr. 1, 1999

(30) Foreign Application Priority Data

Apr. 2, 1998 (DE) .......................................... 198 14 730

(51) Int. Cl.$^7$ ................................................. A61K 9/14
(52) U.S. Cl. ...................... 424/486; 424/484; 424/487; 424/401; 424/422; 514/772; 514/772.2; 514/772.3; 514/772.4
(58) Field of Search .......................... 514/772.5, 772.3, 514/772, 772.1, 772.2, 772.4; 424/484, 486, 487, 401, 422

(56) References Cited

U.S. PATENT DOCUMENTS

| 4,057,623 A | | 11/1977 | Hase et al. ..................... 424/78 |
| 4,057,625 A | * | 11/1977 | Hase et al. ............... 514/772.5 |
| 4,177,056 A | | 12/1979 | Mueller et al. ................. 71/93 |
| 4,304,591 A | | 12/1981 | Mueller et al. ................. 71/93 |
| 4,482,534 A | | 11/1984 | Blank ........................... 424/28 |
| 4,533,540 A | | 8/1985 | Blank ........................... 424/28 |
| 4,801,460 A | * | 1/1989 | Goertz et al. ................ 454/465 |
| 5,073,379 A | * | 12/1991 | Klimesch et al. ............ 424/467 |
| 5,252,611 A | * | 10/1993 | Shih et al. ................ 514/772.5 |
| 6,075,107 A | * | 6/2000 | Kothrade et al. ............ 520/264 |

FOREIGN PATENT DOCUMENTS

| DE | 2514100 | 10/1976 |
| DE | 3810343 | 10/1989 |
| EP | 054279 | 6/1982 |
| EP | 409383 | 1/1991 |
| WO | 89/06957 | 8/1989 |
| WO | WO 97/15293 A2 * | 5/1997 |

* cited by examiner

Primary Examiner—Thurman K. Page
Assistant Examiner—Liliana Di Nola-Baron
(74) Attorney, Agent, or Firm—Keil & Weinkauf

(57) ABSTRACT

The use of copolymers comprising
a) 50 to 99% by weight of at least one N-vinyllactam or N-vinylamine selected from the group consisting of N-vinylpyrrolidone, N-vinylpiperidone, N-vinylcaprolactam, N-vinylimidazole and methylated N-vinylimidazole or N-vinylformamide and
b) 1 to 50% by weight of at least one monomer selected from the group of
   $b_1$) $C_{14}$–$C_{30}$-alkyl esters of monoethylenically unsaturated $C_3$–$C_8$-carboxylic acids;
   $b_2$) N—$C_8$–$C_{30}$-alkyl-substituted amides of monoethylenically unsaturated $C_3$–$C_8$-carboxylic acids;
   $b_3$) N,N—$C_8$–$C_{30}$-dialkyl-substituted amides of monoethylenically unsaturated $C_3$–$C_8$-carboxylic acids;
   $b_4$) vinyl esters of aliphatic $C_8$–$C_{30}$-carboxylic acids;
   $b_5$) $C_8$–$C_{30}$-alkyl vinyl ethers
as matrix for producing solid pharmaceutical and cosmetic presentations.

5 Claims, No Drawings

USE OF N-VINYLLACTAM-OR-N-VINYLAMINE-CONTAINING COPOLYMERS AS MATRIX FOR PRODUCING SOLID PHARAMACEUTICAL AND COSMETIC PRESENTATIONS

The use of N-vinyllactam- or N-vinylamine-containing copolymers as matrix for producing solid pharmaceutical and cosmetic presentations.

The present invention relates to the use of N-vinyllactam- or N-vinylamine-containing copolymers as matrix for producing solid pharmaceutical and cosmetic presentations.

Oral drug forms with a delayed release of active ingredient (slow-release drug forms) are becoming increasingly important. The latter is associated advantageously with improved patient compliance owing to a reduced frequency of intake, a reduction in side effects owing to the avoidance of plasma level peaks, more uniform levels of the medicinal substance in the blood, and the avoidance of local irritation.

Besides coated slow-release forms, i.e. formulation of cores containing medicinal substance and coated with a film which is insoluble in water but semipermeable or contains pores through which the medicinal substance diffuses, it is also possible to achieve control and prolongation of release by embedding the medicinal substance in a matrix.

Embedding the medicinal substance in a matrix offers the particular advantages of simple and low-cost production and high drug safety because dose dumping effects (e.g. the occurrence of high plasma concentrations due to incorrect intake—for example chewing instead of swallowing coated tablets) cannot occur.

The ancillary substances which are usually employed for this, such as hydroxypropylcellulose, hydroxypropylmethylcellulose, alginic acid or alginates, and xanthan, have technical disadvantages on use, however. These derive, on the one hand, from the release of medicinal substance being dependent on the pH or ionic strength and, on the other hand, from the unsatisfactory direct tabletability because, owing to the small binding effect and the poor flow properties of the abovementioned polymers, the resulting compacts frequently have only low hardness or are inhomogeneous.

Since some of the abovementioned ancillary substances are products of natural origin or refined products of natural origin, there may be variations in batch conformity and thus an unfavorable effect on the performance of the pharmaceutical preparation.

DE-A-25 14 100 describes copolymers of vinylpyrrolidone and long-chain alkyl (meth)acrylates, and terpolymers of vinylpyrrolidone, vinyl acetate and long-chain alkyl (meth)acrylates for use as emulsifiers for emulsions of the water-in-oil (W/O) type.

DE-A-38 10 343 describes a process for producing solid slow-release pharmaceutical forms which contain as binder an N-vinylpyrrolidone-containing water-soluble polymer, wherein the pharmaceutical active ingredient, the polymeric binder and, where appropriate, other pharmaceutical ancillary substances are mixed below the glass transition temperature of the binder, and this mixture is compressed above the glass transition temperature of the binder but below the decomposition temperature of the active ingredient to pharmaceutical forms and removed from the mold with the form at a temperature below the glass transition temperature of the binder.

DE-A-25 28 068 describes crosslinked, water-soluble hydrophilic gels consisting, inter alia, of N-vinylpyrrolidone-containing copolymers with various water-insoluble monomers. Water-insoluble monomers which are mentioned are alkyl acrylates and alkyl methacrylates, alkyl having up to 18 C atoms. The polymerization is carried out in bulk or in solution, the active ingredient being present in the reaction medium during the polymerization.

WO 89/06957 describes uncrosslinked copolymers of hydrophilic monomers such as N-vinylpyrrolidone, acrylic acid, methacrylic acid (and their lower esters and hydroxyalkyl esters) and unsaturated linear or branched esters of acrylic acid or methacrylic acid as hydrophobic component for use as binders for active ingredients which are to undergo delayed release. The molar ratio of the monomers is from 1:1.2 to 1:0.8 in the case of N-vinylpyrrolidone/methyl methacrylate.

EP-A-0 054 279 and EP-A-0 409 383 describe the use of water-insoluble, uncrosslinked copolymers of N-vinylpyrrolidone and linear alkyl esters of (meth)acrylic acid in preparations for transdermal administration (ointments, gels) of nitroglycerine or estrogens.

It is an object of the present invention to find polymers which are suitable as matrix for producing solid pharmaceutical and cosmetic preparations with controlled release of active ingredient.

We have found that this object is achieved by using copolymers comprising
  a) 50 to 99% by weight of at least one N-vinyllactam or N-vinylamine selected from the group consisting of N-vinylpyrrolidone, N-vinylpiperidone, N-vinylcaprolactam, N-vinylimidazole and methylated N-vinylimidazole or N-vinylformamide and
  b) 1 to 50% by weight of at least one monomer selected from the group of
    $b_1$) $C_{14}$–$C_{30}$-alkyl esters of monoethylenically unsaturated $C_3$–$C_8$-carboxylic acids;
    $b_2$) N—$C_8$–$C_{30}$-alkyl-substituted amides of monoethylenically unsaturated $C_3$–$C_8$-carboxylic acids;
    $b_3$) N,N—$C_8$–$C_{30}$-dialkyl-substituted amides of monoethylenically unsaturated $C_3$–$C_8$-carboxylic acids;
    $b_4$) vinyl esters of aliphatic $C_8$–$C_{30}$-carboxylic acids;
    $b_5$) $C_8$–$C_{30}$-alkyl vinyl ethers
as matrix for producing solid pharmaceutical and cosmetic presentations.

The following polymerizable comonomers may be mentioned as hydrophilic components a):
  N-vinyllactams and N-vinylamines, in particular N-vinylpyrrolidone, N-vinylpiperidone, N-vinylcaprolactam, N-vinylimidazole, N-vinyl-2-methylimidazole, N-vinyl-4-methylimidazole and N-vinyl formamide.
Preferred hydrophilic components are N-vinylpyrrolidone, N-vinylimidazole and N-vinylcaprolactam, particularly preferably N-vinylpyrrolidone.

The proportion of hydrophilic monomer units a) in the copolymer is in the range from 50 to 99% by weight, preferably 60 to 99% by weight, particularly preferably in the range from 65 to 98% by weight.

The following polymerizable comonomers may be mentioned as hydrophobic components b):
  esters of monoethylenically unsaturated $C_3$–$C_8$-carboxylic acids with a $C_{14}$–$C_{30}$-alcohol, preferably a $C_{14}$–$C_{22}$-alcohol, particularly preferably with a $C_{14}$–$C_{18}$-alcohol.

Monoethylenically unsaturated carboxylic acids with 3 to 8 C atoms mean, for example, acrylic acid, methacrylic acid, dimethylacrylic acid, ethacrylic acid, maleic acid, citraconic acid, methylenemalonic acid, allylacetic acid, vinylacetic acid, crotonic acid, fumaric acid, mesaconic acid and itaconic acid.

Preferably used from this group of carboxylic acids are acrylic acid, methacrylic acid, maleic acid or mixtures of said carboxylic acids, in particular acrylic acid.

Particularly important in this connection are acrylic and methacrylic esters with fatty alcohols of a chain length of from 14 to 22 carbon atoms.

The following may be mentioned here as preferred: myristyl acrylate, cetyl acrylate, stearyl acrylate, oleyl acrylate, behenyl acrylate, myristyl methacrylate, cetyl methacrylate, stearyl methacrylate, oleyl methacrylate, behenyl methacrylate, with the $C_{14}$–$C_{18}$-alkyl esters of acrylic acid being particularly preferred from this group.

Further hydrophobic comonomers b) which can be employed are N—$C_8$–$C_{30}$-alkyl- or N,N—$C_8$–$C_{30}$-dialkyl-substituted amides of monoethylenically unsaturated $C_3$–$C_8$-carboxylic acids, the alkyl radicals being aliphatic or cycloaliphatic alkyl radicals with 8 to 30, preferably 8 to 22, particularly preferably 12 to 18, carbon atoms.

The amidated monoethylenically unsaturated carboxylic acids with 3 to 8 C atoms can, as mentioned above, be, for example, acrylic acid, methacrylic acid, dimethylacrylic acid, ethacrylic acid, maleic acid, citraconic acid, methylenemalonic acid, allylacetic acid, vinylacetic acid, crotonic acid, fumaric acid, mesaconic acid and itaconic acid.

Likewise preferably used from this group of carboxylic acids are acrylic acid, methacrylic acid, maleic acid or mixtures of said carboxylic acids.

Examples of preferred amidated comonomers are N-octylacrylamide, N-2-ethylhexylacrylamide, N-nonylacrylamide, N-decylacrylamide, N-laurylacrylamide, N-myristylacrylamide, N-cetylacrylamide, N-stearylacrylamide, N-oleylacrylamide, N-behenylacrylamide, N-octylmethacrylamide, N-2-ethylhexylmethacrylamide, N-nonylmethacrylamide, N-decylmethacrylamide, N-laurylmethacrylamide, N-myristylmethacrylamide, N-cetylmethacrylamide, N-stearylmethacrylamide, N-oleylmethacrylamide, N-behenylmethacrylamide, with the $C_{12}$–$C_{18}$-alkylamides being particularly emphasized from this group.

It is possible to employ as further additional component b) vinyl esters of long-chain aliphatic, saturated or unsaturated $C_8$–$C_{30}$-carboxylic acids such as, for example, caprylic acid, capric acid, lauric acid, myristic acid, palmitic acid, stearic acid, arachic acid, behenic acid, lignoceric acid, cerotic acid and melissic acid. Vinyl esters of the abovementioned $C_8$–$C_{18}$-carboxylic acids are preferably used.

It is further possible for units of $C_8$–$C_{30}$-alkyl vinyl ethers, preferably $C_8$–$C_{18}$-alkyl vinyl ethers, to be present in the polymer.

Preferred $C_8$–$C_{18}$-alkyl radicals in the vinyl ethers which may be mentioned are unbranched alkyl chains such as, for example, n-octyl, 2-ethylhexyl, n-nonyl, n-decyl, n-undecyl, n-dodecyl, n-tridecyl, n-tetradecyl, n-pentadecyl, n-hexadecyl, n-heptadecyl and n-octadecyl.

The proportion of the hydrophobic monomer units b) in the copolymer is in the range from 1 to 50% by weight, preferably 1 to 40% by weight, particularly preferably in the range from 2 to 35% by weight.

It is, of course, also possible to employ mixtures of two or more carboxylic esters, carboxamides, alkyl vinyl ethers or vinyl esters as long as the total of the proportions of these comonomers does not exceed 50% by weight.

It may be worthwhile, where appropriate, to use, besides the abovementioned monomer units a) and b), for the polymerization the comonomers c) listed below:

monoethylenically unsaturated carboxylic acids with 3 to 8 C atoms such as acrylic acid, methacrylic acid, dimethylacrylic acid, ethacrylic acid, maleic acid, citraconic acid, methylenemalonic acid, allylacetic acid, vinylacetic acid, crotonic acid, fumaric acid, mesaconic acid and itaconic acid. Preferably used from this group of monomers are acrylic acid, methacrylic acid, maleic acid or mixtures of said carboxylic acids.

The monoethylenically unsaturated carboxylic acids can be employed in the copolymerization in the form of the free acid and, if available, the anhydrides or in partially or in completely neutralized form. Preferably used for the neutralization are alkali metal or alkaline earth metal bases, ammonia or amines, e.g. sodium hydroxide solution, potassium hydroxide solution, sodium carbonate, potassium carbonate, sodium bicarbonate, magnesium oxide, calcium hydroxide, calcium oxide, gaseous or aqueous ammonia, triethylamine, ethanolamine, diethanolamine, triethanolamine, morpholine, diethylenetriamine or tetraethylenepentamine.

Further suitable comonomers c) are, for example, the esters, amides and nitriles of the abovementioned carboxylic acids, e.g. methyl acrylate, ethyl acrylate, methyl methacrylate, ethyl methacrylate, hydroxyethyl acrylate, hydroxypropyl acrylate, hydroxybutyl acrylate, hydroxyethyl methacrylate, hydroxypropyl methacrylate, hydroxyisobutyl acrylate, hydroxyisobutyl methacrylate, monomethyl maleate, dimethyl maleate, monoethyl maleate, diethyl maleate, 2-ethylhexyl acrylate, 2-ethylhexyl methacrylate, acrylamide, methacrylamide, N,N-dimethylacrylamide, N-tert-butylacrylamide, acrylonitrile, methacrylonitrile, dimethylaminoethyl acrylate, diethylaminoethyl acrylate, diethylaminoethyl methacrylate and the salts of the last-mentioned monomers with carboxylic acids or mineral acids, and the quaternized products.

Also suitable as other copolymerizable monomers are acrylamidoglycolic acid, vinylsulfonic acid, allylsulfonic acid, methallylsulfonic acid, styrenesulfonic acid, 3-sulfopropyl acrylate, 3-sulfopropyl methacrylate and acrylamidomethylpropanesulfonic acid, and phosphono-containing monomers such as vinylphosphonic acid, allylphosphonic acid and acrylamidomethylpropanephosphonic acid.

The proportion of the monomer units c) in the copolymer can be in the range from 0 to 30% by weight, preferably 0 to 20% by weight, particularly preferably in the range from 0 to 10% by weight, with the % by weight data for components a) to c) totalling 100%.

Water-insoluble copolymers comprising
a) 60–99% by weight of N-vinylpyrrolidone and
b) 1–40% by weight of at least one monomer selected from the group of
  $b_1$) $C_{14}$–$C_{18}$-alkyl esters of monoethylenically unsaturated $C_3$–$C_8$-carboxylic acids;
  $b_2$) N—$C_{12}$–$C_{18}$-alkyl-substituted amides of monoethylenically unsaturated $C_3$–$C_8$-carboxylic acids;
  $b_3$) N,N—$C_{12}$–$C_{18}$-dialkyl-substituted amides of monoethylenically unsaturated $C_3$–$C_8$-carboxylic acids;
  $b_4$) vinyl esters of aliphatic $C_{12}$–$C_{18}$-carboxylic acids;
  $b_5$) $C_8$–$C_{18}$-alkyl vinyl ethers, are preferably used.

The copolymers are prepared by known processes, e.g. of solution, precipitation, emulsion or inverse suspension polymerization, using compounds which form free radicals under the polymerization conditions.

The polymerization temperatures are normally in the range from 30 to 200, preferably 40 to 110° C.

Examples of suitable initiators are azo and peroxy compounds, and the conventional redox initiator systems, such as combinations of hydrogen peroxide and reducing compounds, e.g. sodium sulfite, sodium bisulfite, sodium formaldehyde sulfoxylate and hydrazine.

The copolymers have K values of at least 20, preferably 25 to 100, particularly preferably 30–80. The K values are determined by the method of H. Fikentscher, Cellulose-Chemie, Volume 13, 58 to 64 and 71 to 74 (1932), in aqueous or alcoholic solution at 25° C., with concentrations between 0.1% and 5%, depending on the K value range.

The average molecular weight of the polymers according to the invention is in the range from 30,000 to 10,000,000, preferably 35,000 to 2,000,000, particularly preferably from 40,000 to 1,500,000.

The resulting polymer dispersions or solutions can be converted into powder form by various drying processes such as, for example, spray drying, fluidized spray drying, drum drying or freeze drying, from which powder it is possible to prepare an aqueous dispersion again by redispersion in water.

The polymers are suitable according to the invention as matrix for producing cosmetic and pharmaceutical presentations, in particular solid preparations which can be administered orally, where delayed release of the active ingredient(s) is intended.

The rate of release of the active ingredients can moreover be altered as required as a function of the amount and composition, and of the swelling properties resulting therefrom, of the polymers used according to the invention.

The invention therefore also relates to pharmaceutical and cosmetic preparations comprising as matrix at least one copolymer of
- a) 50 to 99% by weight of at least one N-vinyllactam or N-vinylamine selected from the group consisting of N-vinylpyrrolidone, N-vinylpiperidone, N-vinylcaprolactam, N-vinylimidazole and methylated N-vinylimidazole or N-vinylformamide and
- b) 1 to 50% by weight of at least one monomer selected from the group of
  - $b_1$) $C_{14}$–$C_{30}$-alkyl esters of monoethylenically unsaturated $C_3$–$C_8$-carboxylic acids;
  - $b_2$) N—$C_8$–$C_{30}$-alkyl-substituted amides of monoethylenically unsaturated $C_3$–$C_8$-carboxylic acids;
  - $b_3$) N,N—$C_8$–$C_{30}$-dialkyl-substituted amides of monoethylenically unsaturated $C_3$–$C_8$-carboxylic acids;
  - $b_4$) vinyl esters of aliphatic $C_8$–$C_{30}$-carboxylic acids;
  - $b_5$) $C_8$–$C_{30}$-alkyl vinyl ethers.

Preferred pharmaceutical and cosmetic preparations are those comprising as matrix at least one copolymer of
- a) 60–99% by weight of N-vinylpyrrolidone and
- b) 1–40% by weight of at least one monomer selected from the group of
  - $b_1$) $C_{14}$–$C_{18}$-alkyl esters of monoethylenically unsaturated $C_3$–$C_8$-carboxylic acids;
  - $b_2$) N—$C_{12}$–$C_{18}$-alkyl-substituted amides of monoethylenically unsaturated $C_3$–$C_8$-carboxylic acids;
  - $b_3$) N,N—$C_{12}$–$C_{18}$-dialkyl-substituted amides of monoethylenically unsaturated $C_3$–$C_8$-carboxylic acids;
  - $b_4$) vinyl esters of aliphatic $C_{12}$–$C_{18}$-carboxylic acids;
  - $b_5$) $C_8$–$C_{18}$-alkyl vinyl ethers.

Reference should be made to the description given at the outset for the general and preferred definition of the individual monomer units a) and b) and for the composition and the molecular weight of the copolymers according to the invention.

The solid pharmaceutical or cosmetic preparations according to the invention comprise the copolymer serving as matrix in a concentration of from 0.5 to 90% by weight, preferably 20 to 80% by weight, particularly preferably from 30 to 80% by weight.

The preparations can be produced by methods known per se, inter alia by direct tabletting, dry granulation or wet granulation, and wet extrusion of the copolymers according to the invention with the pharmaceutical or cosmetic active ingredient. A preferred process for producing the solid pharmaceutical or cosmetic preparations is direct tabletting.

Depending on the composition of the copolymers according to the invention it is possible to produce pharmaceutical or cosmetic preparations from which the active ingredients are released within a period of from 0.25 to 24 hours, preferably 0.5 to 20 hours, particularly preferably within 2 to 16 hours.

Pharmaceutical active ingredients which may be mentioned here are, for example, drugs from the group of benzodiazepines, antihypertensives, vitamins, cytostatics, anesthetics, neuroleptics, antidepressants, antibiotics, antimycotics, fungicides, chemotherapeutics, urologicals, platelet aggregation inhibitors, sulfonamides, spasmolytics, hormones, immunoglobulins, sera, thyroid therapeutics, psychopharmaceuticals, antiparkinson agents and other antihyperkinetic agents, ophthalmologicals, neuropathy products, calcium metabolism regulators, muscle relaxants, anesthetics, lipid-lowering agents, liver therapeutics, coronary agents, cardiac agents, immunotherapeutics, regulatory peptides and their inhibitors, hypnotics, sedatives, gynecologicals, antigout agents, fibrinolytics, enzyme products and transport proteins, enzyme inhibitors, emetics, agents promoting blood flow, diuretics, diagnostic agents, corticoids, cholinergics, biliary therapeutics, antiasthmatics, bronchospasmolytics, beta-receptor blockers, calcium channel blockers, ACE inhibitors, antiarteriosclerosis agents, antiinflammatory agents, anticoagulants, antihypotensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, weight-reducing agents.

It is, of course, also possible when formulating the preparations to add other ancillary substances which are customary for producing solid oral presentations.

These may be, inter alia:
bulking agents and binders such as, for example, lactose, calcium phosphates, cellulose and cellulose derivatives, starch and starch derivatives, polyvinylpyrrolidone, polyvinyl alcohol, partially hydrolyzed polyvinyl acetate, sugar alcohols, sugars, fats, waxes;
disintegrants such as, for example, Kollidon® CL (from BASF), Na carboxymethyl starch, Na carboxymethylcellulose;
glidants and lubricants such as, for example, Mg stearate, Ca behenate, stearic acid, PEG;
flow regulators such as, for example, highly disperse silica;
film formers such a s, for example, polyacrylates and polymethacrylates (Eudragit types), copolymers based on acrylate derivatives, hydroxypropylmethylcellulose, hydroxypropylcellulose, cellulose acetate, cellulose acetate phthalate and other enteric coating materials;
humectants such as, for example, glycerol, propylene glycol, sorbitol, mannitol, polyethylene glycols and
plasticizers, colors, surfactants, salts, dispersing aids.

The use of the copolymers according to the invention is explained in detail in the examples which follow.

EXAMPLE 1

160 mg portions of the polymers listed in Table 1 were mixed with 160 mg of propranolol HCl, 3.4 mg of highly disperse silica and 1.6 mg of magnesium stearate and then bevelled tablets were produced directly under a pressure of 18 KN with 10 mm punches.

The release properties of the tablets were tested in a release apparatus (USP XXIII paddle apparatus) at 37° C. with the stirrer rotating at 50 rpm. The active ingredient was released into 900 ml of phosphate buffer pH 7.4 (USP XXIII).

TABLE 1

| Composition | % by weight | K value*) | Release after x min [%] 60 | 240 | 480 | 960 |
|---|---|---|---|---|---|---|
| Vinylpyrrolidone/ stearyl acrylate | 95/5 | 52.4 | 30 | 67 | 92 | — |
| Vinylpyrrolidone/ stearyl acrylate | 95/5 | 41.8 | 55 | 90 | 90 | — |
| Vinylpyrrolidone/ stearyl acrylate | 90/10 | 40.7 | 40 | 90 | 95 | — |
| Vinylpyrrolidone/ stearyl acrylate | 80/20 | 42.7 | 18 | 45 | 80 | 92 |
| Vinylpyrrolidone/ stearyl acrylate | 80/20 | 35.1 | 16 | 47 | 81 | 100 |
| Vinylpyrrolidone/ stearyl acrylate | 90/10 | 35.0 | 40 | 95 | 97 | — |
| Vinylpyrrolidone/ stearyl acrylate | 80/20 | 34.3 | 30 | 85 | 95 | — |
| Vinylpyrrolidone/ stearyl methacrylate | 80/20 | 55.3 | 17.1 | 47.8 | 89.2 | 96.5 |
| Vinylpyrrolidone/ stearyl methacrylate | 70/30 | 46.1 | 12.4 | 38.7 | 57.6 | 80.9 |
| Vinylformamide/ stearyl acrylate | 70/30 | | 22.4 | 38.1 | 53.9 | 71.6 |

*) The K values were determined in ethanol with a polymer concentration of 1% by weight.

We claim:

1. A process for achieving control and prolongation of release of pharmaceutical or cosmetic substances which comprises producing solid pharmaceutical and cosmetic presentations by embedding said pharmaceutical or cosmetic substances in a matrix of copolymer or copolymers consisting essentially of
   a) 50 to 99% by weight of at least one N-vinyllactam or N-vinylamine selected from the group consisting of N-vinylpyrrolidone, -vinylpiperidone, N-vinylcaprolactam, N-vinylimidazole and methylated N-vinylimidazole or N-vinylformamide and
   b) 1 to 50% by weight of at least one monomer selected from the group of
      $b_1$) $C_{14}$–$C_{30}$-alkyl esters of monoethylenically unsaturated $C_3$–$C_8$-carboxylic acids;
      $b_2$) —$C_8$–$C_{30}$-alkyl-substituted amides of monoethylenically unsaturated $C_3$–$C_8$-carboxylic acids;
      $b_3$) N,N—$C_8$–$C_{30}$-dialkyl-substituted amides of monoethylenically unsaturated $C_3$–$C_8$-carboxylic acids;
      $b_4$) $C_8$–$C_{30}$-alkyl vinyl ethers wherein said copolymer comprises 0.5 to 99% by weight of said presentation and from which presentation said pharmaceutical or cosmetic substance is released within a period of from 0.25 to 24 hours.

2. The process of claim 1 wherein said copolymer or copolymers comprise
   a) 60–99% by weight of N-vinylpyrrolidone and
   b) 1–40% by weight of at least one monomer selected from the group of
      $b_1$) $C_{14}$–$C_{22}$-alkyl esters of monoethylenically unsaturated $C_3$–$C_8$-carboxylic acids;
      $b_2$) N—$C_8$–$C_{22}$-alkyl-substituted amides of monoethylenically unsaturated $C_3$–$C_8$-carboxylic acids;
      $b_3$) N,N—$C_8$–$C_{22}$-dialkyl-substituted amides of monoethylenically unsaturated $C_3$–$C_8$-carboxylic acids;
      $b_4$) $C_8$–$C_{18}$-alkyl vinyl ethers.

3. The process of claim 1 wherein said embedding is carried out by direct tabletting, dry or wet granulation, or wet extrusion of said copolymer or copolymers with said pharmaceutical or cosmetic substance.

4. A solid controlled release oral pharmaceutical or cosmetic preparation comprising a pharmaceutical or cosmetic substance embedded in a matrix comprising at least one copolymer of
   a) 50 to 99% by weight of at least one N-vinyllactam or N-vinylamine selected from the group consisting of N-vinylpyrrolidone, N-vinylpiperidone, N-vinylcaprolactam, N-vinylimidazole and methylated N-vinylimidazole or N-vinylformamide and
   b) 1 to 50% by weight of at least one monomer selected from the group of
      $b_1$) $C_{14}$–$C_{30}$-alkyl esters of monoethylenically unsaturated $C_3$–$C_8$-carboxylic acids;
      $b_2$) N—$C_8$–$C_{30}$-alkyl-substituted amides of monoethylenically unsaturated $C_3$–$C_8$-carboxylic acids;
      $b_3$) N,N—$C_8$–$C_{30}$-dialkyl-substituted amides of monoethylenically unsaturated $C_3$–$C_8$-carboxylic acids;
      $b_4$) vinyl esters of aliphatic $C_8$–$C_{30}$-carboxylic acids;
      $b_5$) $C_8$–$C_{30}$-alkyl vinyl ethers;
wherein said copolymer or copolymers comprise 0.5 to 90% by weight of said preparation and from which preparation said pharmaceutical or cosmetic substance is released within a period of from 0.25 to 24 hours.

5. A solid controlled release pharmaceutical or cosmetic preparation as claimed in claim 4, comprising as said matrix at least one copolymer of
   a) 60–99% by weight of N-vinylpyrrolidone and
   b) 1–40% by weight of at least one monomer selected from the group of
      $b_1$) $C_{14}$–$C_{22}$-alkyl esters of monoethylenically unsaturated $C_3$–$C_8$-carboxylic acids;
      $b_2$) N—$C_8$–$C_{22}$-alkyl-substituted amides of monoethylenically unsaturated $C_3$–$C_8$-carboxylic acids;
      $b_3$) N,N—$C_8$–$C_{22}$-dialkyl-substituted amides of monoethylenically unsaturated $C_3$–$C_8$-carboxylic acids;
      $b_4$) $C_8$–$C_{18}$-alkyl vinyl ethers.

* * * * *

UNITED STATES PATENT AND TRADEMARK OFFICE
CERTIFICATE OF CORRECTION

PATENT NO. : 6,436,440 B1
DATED : August 20, 2002
INVENTOR(S) : Meffert et al.

It is certified that error appears in the above-identified patent and that said Letters Patent is hereby corrected as shown below:

Column 8,
Lines 39 and 40, delete the following:
"$b_4$) vinyl esters of aliphatic $C_8$-$C_{30}$-carboxylic acids,
$b_5$)"
and replace it with -- $b_4$) --.

Signed and Sealed this

Fifth Day of November, 2002

*Attest:*

JAMES E. ROGAN
*Attesting Officer*    *Director of the United States Patent and Trademark Office*